United States Patent
Lacheen et al.

(10) Patent No.: US 11,753,355 B2
(45) Date of Patent: Sep. 12, 2023

(54) BASE OIL SYNTHESIS VIA IONIC CATALYST OLIGOMERIZATION AND WATERLESS SEPARATION OF THE OLIGOMERIZATION CATALYST

(71) Applicant: Chevron U.S.A. Inc., San Ramon, CA (US)

(72) Inventors: Howard Steven Lacheen, Richmond, CA (US); Hye-Kyung Cho Timken, Albany, CA (US)

(73) Assignee: CHEVRON U.S.A. INC., San Ramon, CA (US)

( * ) Notice: Subject to any disclaimer, the term of this patent is extended or adjusted under 35 U.S.C. 154(b) by 0 days.

(21) Appl. No.: 16/862,813

(22) Filed: Apr. 30, 2020

(65) Prior Publication Data

US 2022/0041526 A1  Feb. 10, 2022

Related U.S. Application Data

(60) Provisional application No. 62/841,331, filed on May 1, 2019.

(51) Int. Cl.
*C07C 2/12* (2006.01)
*B01J 20/10* (2006.01)
(Continued)

(52) U.S. Cl.
CPC .............. *C07C 2/12* (2013.01); *B01J 20/103* (2013.01); *B01J 20/28061* (2013.01);
(Continued)

(58) Field of Classification Search
CPC ..... C07C 2/12; B01J 20/103; B01J 20/28061; B01J 20/28071; B01J 20/28083;
(Continued)

(56) References Cited

U.S. PATENT DOCUMENTS 5,270,273 A * 12/1993 Pel ........................... C07C 2/12
502/60
5,451,704 A * 9/1995 Ho ....................... B01J 37/0215
585/512
(Continued)

FOREIGN PATENT DOCUMENTS

CN      107207382       9/2017
EP     1044990 A1      10/2000
(Continued)

OTHER PUBLICATIONS

Iler, R.K. (1979) The Chemistry of Silica: Solubility, Polymerization, Colloid and Surface Properties and Biochemistry of Silica, Wiley-Interscience, 866 pp [Office action cites p. 462].*
(Continued)

*Primary Examiner* — Brian A McCaig

(57) ABSTRACT

Described herein is a base oil synthesis via ionic catalyst oligomerization further utilizing a hydrophobic process for removing an ionic catalyst from a reaction mixture with a silica gel composition, specifically a reaction mixture comprising an oligomerization reaction to produce PAO utilizing an ionic catalyst wherein the ionic catalyst is removed post reaction.

24 Claims, 1 Drawing Sheet

(51) Int. Cl.
- *B01J 20/28* (2006.01)
- *B01J 27/125* (2006.01)
- *B01J 31/02* (2006.01)
- *C10G 7/00* (2006.01)
- *C10G 7/06* (2006.01)
- *C10G 25/00* (2006.01)
- *C10G 50/02* (2006.01)
- *C10G 69/12* (2006.01)

(52) U.S. Cl.
CPC ... *B01J 20/28071* (2013.01); *B01J 20/28083* (2013.01); *B01J 27/125* (2013.01); *B01J 31/0284* (2013.01); *C10G 7/003* (2013.01); *C10G 7/06* (2013.01); *C10G 25/003* (2013.01); *C10G 50/02* (2013.01); *C10G 69/126* (2013.01); *C10G 2300/302* (2013.01); *C10G 2300/304* (2013.01); *C10G 2300/70* (2013.01)

(58) Field of Classification Search
CPC ....... B01J 27/125; B01J 31/0284; C10G 7/06; C10G 25/003; C10G 50/02; C10G 69/126; C10G 2300/70; C10G 2300/302; C10G 2300/304
See application file for complete search history.

(56) References Cited

U.S. PATENT DOCUMENTS

| | | |
|---|---|---|
| 2016/0068622 A1 | 3/2016 | Atkins et al. |
| 2016/0168055 A1 | 6/2016 | Buchbinder et al. |
| 2017/0349509 A1* | 12/2017 | Zilbershtein .............. C07C 2/30 |
| 2018/0016204 A1* | 1/2018 | Coffin ....................... C07C 2/06 |

FOREIGN PATENT DOCUMENTS

| | | |
|---|---|---|
| EP | 3237364 A1 | 11/2017 |
| WO | 2017105788 A1 | 6/2017 |
| WO | 2019014540 | 1/2019 |

OTHER PUBLICATIONS

PCT International Search Report and Written Opinion in PCT/IB2020/054104 dated Sep. 14, 2020.

Chinese Office Action, dated Mar. 25, 2023, during the prosecution of CN Application No. 202080042389.X (English Translation).

* cited by examiner

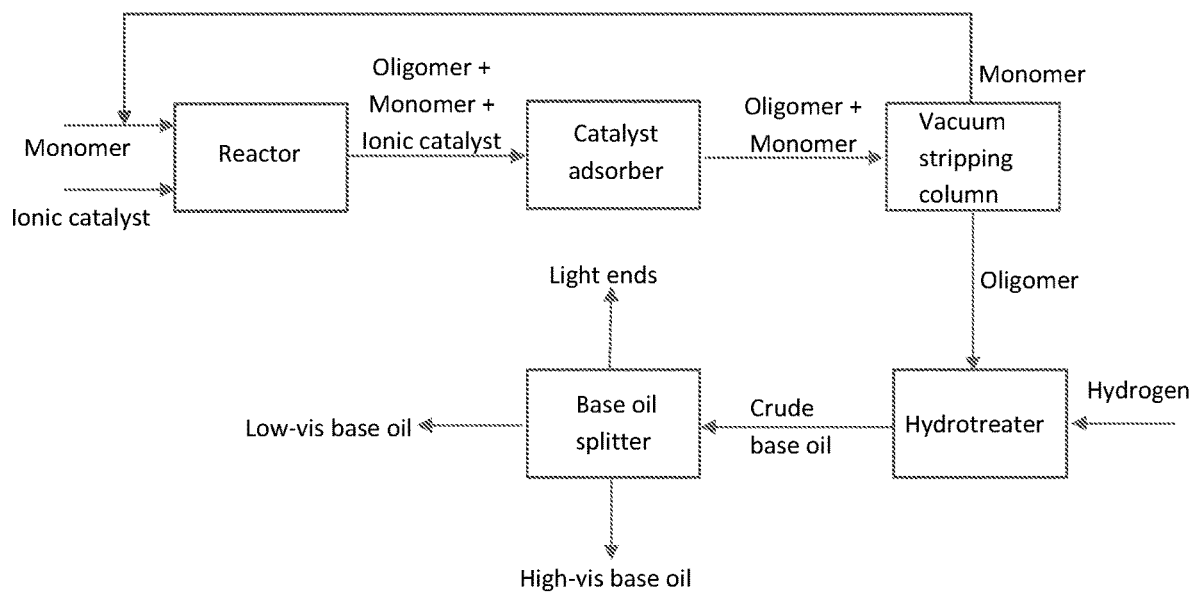

BASE OIL SYNTHESIS VIA IONIC CATALYST OLIGOMERIZATION AND WATERLESS SEPARATION OF THE OLIGOMERIZATION CATALYST

BACKGROUND

Low viscosity poly alpha olefin (PAO) is a premium synthetic base oil produced industrially from $C_{10}$ and $C_{12}$ normal alpha olefins (NAO) with a catalyst system composed of $BF_3$ and alcohol. Due to excellent low temperature flow properties and low volatility, low viscosity PAO is the most desirable blend stock for premium lubricant for higher efficiency engines for automotive applications at this time especially for 0W-20 engine oils.

For the $BF_3$ based processes, the oligomerization reaction is quenched with water where water hydrolyzes and deactivates the $BF_3$ catalyst. Then the hydrocarbon product is washed further with water to remove the residual $BF_3$ catalyst from the hydrocarbon phase. These quenching and washing steps generate a large amount of hazardous aqueous waste and it is typically disposed via deep well injection.

This PAO is very expensive and the supply is limited. Therefore, there remains a need for an alternate process of making a base oil composition having properties comparable to those from the $BF_3$ processes, and for the alternate manufacturing process generating lesser amount of hazardous waste materials.

Recently, chloroaluminate ionic liquids have shown potential to catalyze the hydrocarbon conversion processes. Ionic liquids have been used to catalyze a variety of hydrocarbon conversion processes, such as alkylation, isomerization, disproportionation, and oligomerization. Ionic liquids are essentially salts in a liquid state, and are described in U.S. Pat. Nos. 4,764,440, 5,104,840, and 5,824,832. U.S. Pat. No. 7,527,944, herein incorporated by reference, discloses the use of ionic liquids as catalysts for the cationic polymerization of alpha-olefins.

Ionic liquids are a class of compounds that have been developed over the last few decades. The term "ionic liquid" as used herein refers to a liquid that can be obtained by melting a salt, and which is composed entirely of ions. The term "ionic liquid" includes compounds having both high melting points and compounds having low melting points, e.g. at or below room temperature. Ionic liquids having melting points below around 30° C. are commonly referred to as "room temperature ionic liquids" and are often derived from organic salts having nitrogen-containing heterocyclic cations, such as imidazolium and pyridinium-based cations or from quaternary alkyl amine organic salts or quaternary alkyl phosphonium organic salts.

The ionic liquid catalysts disclosed by U.S. Pat. No. 7,572,944 comprise pyridinium or imidazolium cations together with chloroaluminate anions. The use of ionic liquids as polymerization catalysts is known to provide certain advantages over conventional catalysts. In particular, ionic liquids are generally immiscible with hydrocarbons and thus can be separated from polyalphaolefin products by phase separation and recycled.

When ionic liquids are used to catalyze hydrocarbon conversion processes, the hydrocarbon feed and the ionic liquid catalyst are typically mixed with high shear to provide intimate contact. During the mixing, small droplets of ionic liquid become suspended in the immiscible, hydrocarbon phase. Some of these small droplets of ionic liquid remain entrained in the immiscible phase after conventional liquid-liquid phase separation by gravity. Since ionic liquids have a relatively high cost associated therewith, it is important to recover this entrained ionic liquid. The entrained ionic liquid can be separated using a coalescer as described in U.S. Pat. No. 8,067,656.

U.S. Pat. No. 10,435,491, disclosed that ionic liquid catalyst in combination with organic chloride shifts the molecular weight of oligomer product toward lighter boiling range oligomers, with an average molecular weight of oligomer product from 400 to 800 grams/mol.

In a patent application co-filed with this application, we described the use of a chloroaluminate ionic liquid catalyst or ionic complex catalyst that can make premium base oil using high carbon number normal alpha olefins ($C_{14}$-$C_{24}$) which is cheaper than $C_{10}$ and $C_{12}$ NAO used in the current commercial processes. $C_{14}$-$C_{24}$ NAO can be produced from petroleum source as well as bio-based sources such as natural triglycerides and fatty acids, thus will be more readily available. In this process, the chemical reaction is controlled to maximize the dimer yield and to minimize higher molecular weight oligomers comprising trimers and higher.

After the oligomerization reaction, the ionic catalyst needs to be separated from the reaction mixture containing oligomer product and unreacted olefin monomer for further processing. The solubility of ionic catalysts in olefins or oligomers are rather high in that physical separation alone, via gravity or centrifuge or hydrocyclone separation that removes entrained immiscible ionic liquid, will produce the hydrocarbon phase still containing rather a high amount of ionic catalyst (order of hundreds of ppm). Carry-over of ionic catalyst to the downstream process would cause negative consequences such as contamination or degradation of the hydrocarbon product, or corrosion in the downstream equipment. Thus, effective removal of ionic catalyst from the reaction product is necessary.

One way of removing the ionic catalyst from the oligomerization reaction product is water quenching followed by washing, similar to the $BF_3$-based PAO process. After the oligomerization reaction, the reaction mixture, containing unconverted monomer, oligomerized product and the ionic catalyst, is typically added to water or aqueous solution to quench the catalytic reaction. During the water quenching, the ionic catalyst is hydrolyzed and moved to the aqueous phase. Then aqueous phase containing the hydrolyzed catalyst is separated from the hydrocarbon phase and discarded. The washing and separation steps are repeated until the hydrocarbon phase is virtually free of the ionic catalyst. Mixing of the oligomerization reaction product with aqueous solutions or water can form emulsions of oil and water and rag layers. Each washing step is time consuming and/or requiring coalescer as the washed mixture needs to be in a separation vessel long enough time until the emulsions are separated into clear hydrocarbon phase and aqueous phase by gravity and/or via coalescing.

Formation of some emulsion causes water trapped in the hydrocarbon phase and needs to be removed. A drying agent, such as $MgSO_4$ powders, is added to the wet hydrocarbon phase and then filtered out. Alternatively, the wet hydrocarbon phase is passed through a fixed bed containing dryerant pellets.

These washing and drying steps cause some loss of precious hydrocarbon product through the rag layer, and some loss of hydrocarbon to the water phase and to the drying agent. In addition, these washing and drying steps generate a large amount of water waste and solid waste. Also, there is a risk of insufficient drying of hydrocarbon which may cause water carry-over via recycling of unconverted monomer to the oligomerization reactor, damaging the oligomerization catalyst and/or causing corrosion in process equipment.

A more efficient process for removing ionic catalyst from the reaction mixture is desired. It is desirable for the removal process has a reduced loss of the hydrocarbon product and smaller amount of waste generation.

SUMMARY OF THE INVENTION

An embodiment of the invention is a base oil synthesis via ionic catalyst oligomerization further utilizing a hydrophobic process for removing an ionic catalyst from a reaction mixture with a silica gel composition, specifically a reaction mixture comprising an oligomerization reaction to produce PAO utilizing an ionic catalyst wherein the ionic catalyst is removed post reaction.

BRIEF DESCRIPTION OF THE DRAWINGS

FIG. 1 is a block diagram for Premium Base Oil Manufacturing from $C_{14}$-$C_{24}$ NAO.

DESCRIPTION OF THE INVENTION

Herein is described a process for removing ionic catalyst from a reaction mixture with a silica gel composition, specifically a reaction mixture comprising an oligomerization reaction to produce oligomers utilizing an ionic catalyst wherein a water washing is not required to remove the catalyst.

The process as herein described has the following advantages compared to the conventional aqueous solution washing process: (1) Reducing the loss of the hydrocarbon product, (2) less waste generation, (3) removing the process step of aqueous washing to remove the catalyst-improving the overall economy of the process, (4) more efficient in that a lower amount of residual ionic catalyst is present in the hydrocarbon phase.

An embodiment of the invention is a hydrophobic process for separating oligomerization products from a liquid catalyst post oligomerization reaction comprising reacting an olefin monomer and liquid catalyst in a reactor to form an oligomer, (b) contacting the mixture comprising liquid catalyst and formed oligomer with a silica gel wherein the silica gel is about 1-20 wt % (c) retaining the liquid catalyst in the silica gel and (d) producing an oligomer product with residual liquid catalyst.

An additional embodiment of the invention is the oligomerization reaction occurring in a continuous stirred tank reactor or in a batch reactor.

An additional embodiment of the invention is the hydroisomerization reaction of the oligomer product to produce premium quality, low-viscosity base oil.

Feed Stock

Feed stock is comprised of normal alpha olefins with the carbon number ranging from 6 to 24 ($C_6$-$C_{24}$), preferentially $C_{10}$-$C_{18}$ from petroleum process or from bio-derived alpha olefins or from wax cracking. Feed stock may contain lower carbon number normal alpha olefins in the range of $C_6$-$C_{12}$ up to 40 wt % and may contain paraffins in the carbon number range of $C_6$-$C_{20}$ up to 10 wt %.

Olefin Oligomerization

In a particular embodiment of the process for $C_{14}$-$C_{24}$ oligomerization, the chemical reaction is controlled to maximize the dimer yield and to minimize higher molecular weight oligomers (trimer, tetramers and higher oligomers). Oligomerization may be by semi-batch or continuous mode in a suitable reactor. A particular embodiment is the conversion of hexadecene to oligomer, wherein the percent conversion is in the range of 40% to 85%. A particular embodiment is the selectivity of dimer (low-viscosity oil), wherein the percent selectivity of the low-viscosity oil is in the range of 50% to 90%.

The conditions for oligomerization are tailored to maximize the dimer yield (low-viscosity oil) and to produce partially isomerized oligomer for hydroisomerization. The reaction temperature is generally between about 100° C. and 250° C., preferably between 130° C. to 200° C., at a residence time generally between about 5 minutes and about 2 hr, preferably between about 10 minutes and about 2 hr. The amount of ionic catalyst in the reactor is generally between 0.01 and 10 vol %, preferably between 0.02 and 5 vol % and most preferably between 0.05 and 1 vol %. The pressure is typically from about atmospheric pressure (0 psig) to about 600 psig, preferably from about 10 psig to about 400 psig, and most preferably from about 20 psig to about 200 psig. High temperature, above 130° C. or higher enhanced low-viscosity oil selectivity and isomerization of oligomer product, which allows milder hydroisomerization finishing. HCl co-feeding is required for the ionic liquid catalyst wherein the olefin to HCl molar ratio is generally between 15:1 and 400:1, preferably between 30:1 and 200:1. HCl co-feeding is not required for ionic complex catalyst.

An embodiment includes an ionic liquid catalyst with HCl co-feeding with 30:1-200:1 olefin to HCl ratio is the preferred process for the olefin oligomerization of $C_{14}$-$C_{24}$ NAO. A further embodiment includes and an ionic complex catalyst without HCl addition is the most preferred process for the olefin oligomerization of $C_{14}$-$C_{24}$ NAO.

In one embodiment, the reaction mixture is distilled to remove the unreacted monomer. For example, the unreacted monomer may be separated from the oligomer product, such as via distillation, and can be recycled back into the mixture of the first and/or second feedstocks for oligomerization thereof.

Ionic Catalysts

Ionic catalyst as described herein encompasses both ionic liquid catalysts, ionic complex catalysts and ionic liquid catalyst with HCl co-catalyst. The ionic liquid catalyst is made of anhydrous metal halides and amine salts. $AlCl_3$, $AlBr_3$, $GaCl_3$ or $GaBr_3$ are preferred metal halides. Alkyl ammonium halides and alkyl phosphonium halides are preferred amine salts. Ionic complex catalyst made of anhydrous metal halides (Lewis acid) and molecules with strong electron donor atoms that will act as Lewis base with the anhydrous metal chlorides. $AlCl_3$, $AlBr_3$, $GaCl_3$ or $GaBr_3$ are preferred metal halides. Urea, thiourea, alkyl amides and alkyl phosphines are preferred molecules.

The ionic liquid comprises an organic cation and an anion. Suitable cations include, but are not limited to, nitrogen-containing cations and phosphorus-containing cations. The ionic liquid can comprise phosphonium based ionic liquids, pyridinium based ionic liquids, imidazolium based ionic liquids, ammonium based ionic liquids, pyrrolidinium based ionic liquids, and lactamium based ionic liquids. Ammonium based ionic liquids include trialkyl and tetra alkyl ammonium based ionic liquids.

In some embodiments, the anion can be derived from halides, typically halometallates, and combinations thereof. The anion is typically derived from metal and nonmetal halides, such as metal and nonmetal chlorides, bromides, iodides, fluorides, or combinations thereof. Combinations of halides include, but are not limited to, mixtures of two or more metal or nonmetal halides (e.g., $AlCl_4^-$ and $BF_4^-$), and mixtures of two or more halides with a single metal or nonmetal (e.g., $AlCl_3Br^-$). Suitable anions include, but are not limited to, $AlCl_4^-$, $Al_2Cl_7^-$, $Al_3Cl_{10}^-$, $AlBr_4^-$, $Al_2Br^-$, $GaCl_4^-$, $Ga_2Cl_7^-$, $Ga_3Cl_{30}^-$, $CuCl_2^-$, $Cu_2Cl_3^-$, $ZnCl_3^-$, $FeCl_3^-$, $FeCl_4^-$, $Fe_3Cl_7^-$, $PF_6^-$, and $BF_4^-$. In other embodiments, other anions could be used.

The preferred ionic liquid composition is 2 moles of anhydrous metal chlorides to 1 mole of amine chloride. Mixing of these two ionic materials forms ionic liquid made of entirely cations and anions.

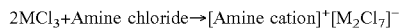

$$2MCl_3 + \text{Amine chloride} \rightarrow [\text{Amine cation}]^+ [M_2Cl_7]^-$$

where M is a metal selected from aluminum, gallium, and indium. To improve the selectivity of the ionic liquid catalyst to low-viscosity base oil, presence of anhydrous HCl co-catalyst is required as reported in U.S. Pat. No. 10,435,491, herein incorporated by reference.

An embodiment of the invention includes an ionic liquid wherein the ionic liquid composition is 2 moles of anhydrous metal chlorides to 1 mole of amine chloride including those modified slightly to 1.8:1 of anhydrous metal chlorides to 1 mole of amine chloride.

A preferred embodiment is the use of anhydrous gallium chloride containing ionic liquid catalyst demonstrating higher selectivity than the aluminum chloride containing catalyst.

An embodiment is the invention includes addition of anhydrous HCl gas to the oligomerization mixture containing ionic liquid catalyst to maximize the dimer production, wherein the percent low-viscosity oil selectivity is in the range of 40% to 85%.

A further embodiment includes an ionic complex catalyst used for the olefin oligomerization of $C_{14}$-$C_{24}$ NAO. The class of ionic complex catalyst is a homogeneous molten liquid at ambient temperature made from 3:2 molar ratio of anhydrous, Lewis-acid metal halides and Lewis-base.

Anhydrous Lewis-acid halides such as $AlCl_3$, $GaCl_3$, $InCl_3$, $AlBr_3$, $AlI_3$, $GaBr_3$, $GaI_3$, $InBr_3$ and $In_3$ can be used to make the ionic complex catalyst. Suitable solid Lewis-bases include molecules containing atoms with electron pair such as oxygen, phosphorus, sulfur, nitrogen. Examples of Lewis-bases include lutidine, collidine, alkylpyridines, trioctylphosphine, alkylphosphines, trioctylphosphine oxide, alkylphosphine oxides, ureas (e.g., N,N'-dimethyl urea, N,N'-diethyl urea), thioureas (e.g., thiourea, N-methylthiourea, N,N'-dimethylthiourea, N-ethylthiourea, N,N'-diethylthiourea), amides (e.g., acetamide, propionamide, benzamide), dialkyacetamides, alkylamides, octanenitrile, and alkylnitriles. When these two solids ingredients (strong Lewis-acid and Lewis-base) in powder form are mixed in 3:2 molar ratio, their strong interaction induces deep eutectic behavior to the combined solid powders, and the mixture becomes liquid at the ambient temperature.

An embodiment is the invention includes no addition of anhydrous HCl gas to the oligomerization mixture containing ionic complex catalyst to maximize the dimer production, wherein the percent low-viscosity oil selectivity is in the range of 40% to 85%.

Without being bound by any theory, it is believed addition of a strong Lewis donor ligand to a Group 13 metal halide results in disproportionation of the metal species into cationic and anionic ionic complexes which exists in equilibrium with neutral complexes, such as described in the following equation:

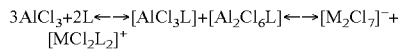

$$3AlCl_3 + 2L \leftrightarrow [AlCl_3L] + [Al_2Cl_6L] \leftrightarrow [M_2Cl_7]^- + [MCl_2L_2]^+$$

where M is a metal selected from aluminum, gallium and indium; X is a halides selected from chloride, bromide, and iodide; and L represents a Lewis basic donor ligand. The eutectic behavior (becoming liquid) may be coming from ionic species formation.

Silica Gel

As described above the state of the art for removal of the ionic catalyst from the oligomerization reaction product is water quenching followed by washing and drying to attain the final hydrocarbon product, wherein these subsequent washing and drying steps cause loss of hydrocarbon product through the rag layer, water phase and to the drying agent. In addition, these washing and drying steps generate a large amount of water waste and solid waste. Also, there is a risk of insufficient drying of hydrocarbon which may cause water carry-over via recycling of unconverted monomer to the oligomerization reactor, damaging the oligomerization catalyst and/or causing corrosion in process equipment.

An embodiment of the invention is the use of a high-purity grade silica gel with 99% or higher assay used as the filtration agent for removing the ionic liquid or ionic complex catalyst to eliminate the added steps and complications associated with water quenching, washing and drying. Silica gel $mSiO_2 \cdot nH_2O$, is a highly active, porous material with the internal surface area being large. Generally, the specific surface area can reach above 200 $m^2$ per g silica. Specific characteristics of silica gel employed herein is silica gel which has an average pore diameter about 30 Å to about 1000 Å, a mesopore (25-1000 Å) pore volume of about 0.2 cc/g to about 2 cc/g and a surface area of about 100 $m^2/g$ to about 500 $m^2/g$. A preferred embodiment is the use of high purity silica gel. Examples 6 and 7 below, while not limiting the teachings herein provide exemplary support.

Treatment with 1-20 wt % of silica-gel selectively removes nearly completely the ionic catalyst in the reaction mixture in one step in the absence of a water washing typically used to remove the ionic catalyst. The final product has reduced residual catalyst impurities than those prepared with multiple washings followed by drying, wherein the residual liquid catalyst content is less than 50 ppm, preferably less than 20 ppm, most preferably less than 2 ppm.

Hydroisomerization

As a finishing step, the oligomer product is hydrogenated with a hydrogenation catalyst in the presence of hydrogen at an elevated pressure to make fully saturated base oil. Heterogeneous, hydrogenation catalyst containing nickel is commonly used for PAO hydrogenation. Precious metal, such as Pt, Pd, or Ru, supported catalyst can also be used for hydrogenation of oligomers.

Hydroisomerization catalysts useful in the present invention usually comprises a shape-selective molecular sieve, a metal or metal mixture that is catalytically active for hydrogenation, and a refractory oxide support. The presence of a hydrogenation component leads to improvement in product stability. Typical catalytically active hydrogenation metals include chromium, molybdenum, nickel, vanadium, cobalt, tungsten, zinc, platinum, and palladium. Platinum and palladium are especially preferred, with platinum mostly preferred. If platinum and/or palladium is used, the metal content is typically in the range of 0.1 to 5 weight percent of the total catalyst, usually from 0.1 to 2 weight percent, and not to exceed 10 weight percent. Hydroisomerization catalysts are discussed, for example, in U.S. Pat. Nos. 7,390,763 and 9,616,419, as well as U.S. Patent Application Publications 2011/0192766 and 2017/0183583.

Platinum and palladium and ruthenium may be the preferred metals for hydroisomerization. Other Group VIII transition metals such as Ni, Co, Fe, W, Re, Os or Ir may be used for the process. Zeolite containing one-dimensional or two-dimensional, 10-membered ring pore structure, such as those having MFI, MEL, MFS, MRE, MTT, SFF, STI, TON, OSI, or NES framework type may be used. Suitable zeolites include ZSM-5, ZSM-11, ZSM-23, ZSM-35, ZSM-48, ZSM-57, SSZ-32, SSZ-35, SSZ-91, SSZ-95, SSZ-109, NU-87, ALPO-31, SAPO-11.

Amorphous materials with acidic sites in combination with metal may be used for hydroisomerization. Suitable amorphous materials include amorphous silica-alumina, silica-alumina-titania, zirconia-alumina and zirconia-ceria-alumina.

The conditions for hydroisomerization are tailored to achieve an isomerized hydrocarbon mixture with specific branching properties, and thus will depend on the characteristics of feed used. The reaction temperature is generally between about 200° C. and 400° C., preferably between 250° C. to 370° C., most preferably between 260° C. to 345° C., at a liquid hourly space velocity (LHSV) generally between about 0.1 $hr^{-1}$ and about 5 $hr^{-1}$, preferably between about 0.2 $hr^{-1}$ and about 3 $hr^{-1}$ The pressure is typically from about 15 psig to about 2500 psig, preferably from about 50 psig to about 2000 psig, more preferably from about 100 psig to about 1500 psig, most preferably 100 to 800 psig.

Low pressure provides enhanced isomerization selectivity, which results in more isomerization and less cracking of the feed, thus leading to an increased yield of hydrocarbon mixture in the base stock boiling range. Hydrogen is present in the reaction zone during the hydroisomerization process, typically in a hydrogen to feed ratio from about 0.1 to 10 MSCF/bbl (thousand standard cubic feet per barrel), preferably from about 0.3 to about 5 MSCF/bbl. Hydrogen may be separated from the product and recycled to the reaction zone.

The hydroisomerized product was distilled to produce three fractions, 700° F.-(371° C.) light fraction, low-viscosity base oil cut (700-910° F. or 371-488° C.) and high-viscosity base oil cut (910° F.$^+$ or 488° C.$^+$). The low-viscosity cut in the 700-910° F. (371-488° C.) boiling range is mainly made of dimer product and high-viscosity cut in 910° F.$^+$ (488° C.$^+$) boiling range contains trimer, tetramers and higher oligomers.

Product Properties for Premium Base Oil

The low-viscosity fraction contains predominately the dimers and a small amount of trimers. The high-viscosity fraction contains mostly trimer and tetramers.

The oligomer products made from high carbon number, normal alpha olefins ($C_{14}$-$C_{24}$) have very high viscosity index (VI) of over 150, well exceeding the target VI of above 130. However, the dimer products have major drawbacks for low temperature performances. The oligomer products are waxy and show poor low temperature properties of pour and cloud points.

We improved the base oil properties further by substituting the hydrogenation finishing step with a hydroisomerization finishing process as set forth above with a preferred embodiment being the use of a medium pour zeolite catalyst.

The oligomerized product was hydroisomerized under the $H_2$ atmosphere with a catalyst containing precious metal and medium pore zeolite to saturate the double bonds in the olefin oligomers and isomerize the carbon backbone structure at the same time. The resulting products met all target properties of the premium low-vis base oil (see Table 1 for target properties). No additional, subsequent hydrogenation step is required.

To meet the performance requirement as well as meeting the environmental requirements, the desirable base oil properties are low-viscosity, high viscosity index (VI), low pour and cloud point, low Noack volatility, and low temperature cold crank simulator (CCS) viscosity.

While not being limited to the base oil properties exemplified below, "Base Oil" as used herein refers to the premium base oil as described herein used to manufacture products including dielectric fluids, hydraulic fluids, compressor fluids, engine oils, lubricating greases or formulations, and metal processing fluids.

The base oil disclosed herein can be used as lubricant base stocks to formulate final lubricant products comprising additives. In certain variations, a base stock prepared according to the methods described herein is blended with one or more additional base stocks, e.g., one or more commercially available PAOs, a Gas to Liquid (GTL) base stock, one or more mineral base stocks, a vegetable oil base stock, an algae-derived base stock, a second base stock as described herein, or any other type of renewable base stock. Any effective amount of additional base stock may be added to reach a blended base oil having desired properties. For example, blended base oils can comprise a ratio of a first base stock as described herein to a second base stock (e.g., a commercially available base oil PAO, a GTL base stock, one or more mineral base stocks, a vegetable oil base stock, an algae derived base stock, a second base stock as described herein) that is about is from about 1-99%, from about 1-80%, from about 1-70%, from about 1-60%, from about 1-50%, from about 1-40%, from about 1-30%, from about 1-20%, or from about 1-10%, based on the total weight of the composition may be made.

Also disclosed herein are lubricant compositions comprising a hydrocarbon mixture described herein. In some variations, the lubricant compositions comprise a base oil comprising at least a portion of a hydrocarbon mixture produced by any of the methods described herein, and one or more additives selected from the group of antioxidants, viscosity modifiers, pour point depressants, foam inhibitors, detergents, dispersants, dyes, markers, rust inhibitors or other corrosion inhibitors, emulsifiers, de-emulsifiers, flame retardants, antiwear agents, friction modifiers, thermal stability improvers, multifunctional additives (e.g., an additive that functions as both an antioxidant and a dispersant) or any combination thereof. Lubricant compositions may comprise hydrocarbon mixtures described herein and any lubricant additive, combination of lubricant additives, or available additive package.

Any of the compositions described herein that are used as a base stock may be present at greater than about 1% based on the total weight of a finished lubricant composition. In certain embodiments, the amount of the base stock in the formulation is greater than about 2, 5, 15 or 20 wt % based on the total weight of the formulation. In some embodiments, the amount of the base oil in the composition is from about 1-99%, from about 1-80%, from about 1-70%, from about 1-60%, from about 1-50%, from about 1-40%, from about 1-30%, from about 1-20%, or from about 1-10% based on the total weight of the composition. In certain embodiments, the amount of base stock in formulations provided herein is about 1%, 5%, 7%, 10%, 13%, 15%, 20%, 30%, 40%, 50%, 60%, 70%, 80%, 90%, or 99% based on total weight of the formulation.

As is known in the art, types and amounts of lubricant additives are selected in combination with a base oil so that the finished lubricant composition meets certain industry standards or specifications for specific applications. In general, the concentration of each of the additives in the composition, when used, may range from about 0.001 wt. % to about 20 wt. %, from about 0.01 wt. % to about 10 wt. %, from about 0.1 wt. % to about 5 wt. % or from about 0.1 wt. % to about 2.5 wt. %, based on the total weight of the composition. Further, the total amount of the additives in the composition may range from about 0.001 wt. % to about 50 wt. %, from about 0.01 wt % to about 40 wt %, from about 0.01 wt % to about 30 wt %, from about 0.01 wt. % to about 20 wt. %), from about 0.1 wt. % to about 10 wt. %, or from about 0.1 wt. % to about 5 wt. %, based on the total weight of the composition.

In some variations, the base oils described herein are formulated in lubricant compositions for use as two cycle engine oils, as transmission oils, as hydraulic fluids, as compressor oils, as turbine oils and greases, as automotive engine oils, as gear oils, as marine lubricants, and as process oils. Process oils applications include but are not limited to: rolling mill oils, coning oils, plasticizers, spindle oils, polymeric processing, release agents, coatings, adhesives, sealants, polish and wax blends, drawing oils, and stamping oils, rubber compounding, pharmaceutical process aids, personal care products, and inks.

In yet other variations, the base oils described herein are formulated as industrial oil or grease formulations comprising at least one additive selected from anti-oxidants, anti-wear agents, extreme pressure agents, defoamants, detergent/dispersant, rust and corrosion inhibitors, thickeners, tackifiers, and demulsifiers. It is also contemplated that the base stocks of the invention may be formulated as dielectric heat transfer fluids composed of relatively pure blends of compounds selected from aromatic hydrocarbons, polyalphaolefins, polyol esters, and natural vegetable oils, along with additives to improve pour point, increase stability and reduce oxidation rate.

Premium base oil properties described herein are as follows (Table 1):

TABLE 1

Target Properties for Premium Base Oil Synthesis from NAO

|  | Low-Viscosity Base Oil Cut | High-Viscosity Base Oil Cut |
|---|---|---|
| Viscosity at 100° C. | 3.5-4.6 cSt | 4.7 or higher |
| Noack volatility | <15% | — |
| Viscosity index | >130 | >130 |
| Pour point | <−20° C. | <−10° C. |
| Cloud point | <−10° C. | <0° C. |
| Cold crank simulator viscosity at −35° C. | <2500 cP | — |
| Mini-rotary viscometer viscosity at −40° C. | <60,000 cP | — |

Example 1: Ionic Liquid Catalyst, N-butylpyridinium chloroaluminate ($C_5H_5NC_4H_9Al_2Cl_7$, Abbreviated as [BuPy][$Al_2Cl_7$])

N-butylpyridinium chloroaluminate was synthesized in a glove box under $N_2$ atmosphere by slowly mixing 2:1 mole ratio of anhydrous $AlCl_3$ powers and dried N-butylpyridinium chloride powers together. Slight heat was applied to ~50° C. while stirring, and the mixture became liquid. Then a small fraction of each solid at a time was added alternately to the beaker to continue to make the molten liquid until all ingredients are added and dissolved well. Continued the stirring of the liquid overnight and then filtered it with a fine frit to remove any residual solid. The composition of this ionic liquid catalyst is shown in Table 2.

Example 1-2: N-butylpyridinium chloroaluminate (Abbreviated as [BuPy][1.8 $Al_2Cl_7$])

This ionic liquid was synthesized using the procedure of Example 1-1 and the same starting material. However, the molar ratio of the anhydrous $AlCl_3$ and N-butylpyridinium chloride is 1.8:1. This lowers the acidity of the catalyst slightly and improves the dimer selectivity.

Example 1-3: Ionic Liquid Catalyst with Anhydrous Gallium Chloride, N-butylpyridinium chlorogallate ($C_5H_5NC_4H_9Ga_2Cl_7$, Abbreviated as [BuPy][$Ga_2Cl_7$])

N-butylpyridinium chlorogallate was synthesized in a glove box under $N_2$ atmosphere by slowly mixing 2:1 mole ratio of anhydrous $GaCl_3$ powers and dried N-butylpyridinium chloride powers together. Slight heat was applied to ~50° C. while stirring, and the mixture became liquid. Then a small fraction of each solid at a time was added alternately to the beaker to continue to make the molten liquid until all ingredients are added and dissolved well. Continued the stirring of the liquid overnight and then filtered it with a fine frit to remove any residual solid.

TABLE 2

Composition of Ionic Catalysts

| Element, wt % | Ionic Liquid Catalyst [BuPy][$Al_2Cl_7$] Example 1 | Ionic Complex Catalyst Acetamide-$AlCl_3$ Example 2-1 | Ionic Complex Catalyst Urea-$AlCl_3$ Example 2-2 |
|---|---|---|---|
| Al | 12.4 | 15.3 | 15.3 |
| Cl | 56.5 | ~61 | 59.9 |
| C | 24.6 | 10.0 | 5.3 |
| H | 3.2 | 2.3 | 2.0 |
| N | 3.3 | 5.6 | 11.4 |

Example 2-1: Synthesis of Ionic Coordination Complex of $AlCl_3$ and Acetamide (Acetaminde-$AlCl_3$)

An ionic complex made of 3:2 molar ratio of anhydrous aluminum chloride and acetamide was prepared by using 413.9 g of anhydrous $AlCl_3$ and 122.1 g of acetamide ($CH_3CONH_2$). As-received acetamide was dried in a vacuum oven at 70° C. overnight. Anhydrous aluminum chloride was used as-received. The synthesis was done in a glove box. About 1/20 of the amount of aluminum chloride and acetamide powders were mixed in a beaker with a magnetic stirrer. Slight heat was applied to ~50° C. while stirring, and the mixture became liquid. Then about 1/20 fraction of each solid at a time was added alternately to the beaker to continue to make the molten liquid until all ingredients are added and dissolved well. Continued the stirring of the liquid overnight and then filtered it with a fine frit to remove any residual solid. The composition of this ionic complex catalyst is shown in Table 2.

Example 2-2: Synthesis of Ionic Complex Catalyst of $AlCl_3$ and Urea (Urea-$AlCl_3$)

An ionic complex made of 3:2 molar ratio of anhydrous aluminum chloride and urea was prepared by using 480.6 g of anhydrous AlCl$_3$ and 144.1 g of urea (H$_2$NCONH$_2$). As-received urea was dried in a vacuum oven at 80° C. overnight. Anhydrous aluminum chloride was used as-received. The synthesis was done in a glove box. About 1/20 of the amount of aluminum chloride and urea powders were mixed in a beaker with a magnetic stirrer. Slight heat was applied to ~50° C. while stirring, and the mixture became liquid. Then about 1/20 fraction of each solid at a time was added alternately to the beaker to continue to make the molten liquid until all ingredients are added and dissolved well. Continued the stirring of the liquid overnight and then filtered it with a fine frit to remove any residual solid. The composition of this ionic complex catalyst is shown in Table 6.

Example 3: Olefin Oligomerization and Ionic Catalyst Removal with Aqueous Wash (Comparative Example n-Hexadecene normal alpha olefin (C$_{16}$ NAO) was oligomerized using [BuPy][Al$_2$Cl$_7$] ionic liquid catalyst from Example 1-1. Oligomerization was run in a continuous unit with 0.2 vol % of ionic liquid catalyst. A small amount of HCl co-catalyst was added. The oligomerization temperature performed was 130° C.

The reaction product containing ionic liquid catalyst, oligomers and unreacted C$_{16}$ NAO were washed with equal parts by volume dilute 2.5 pH hydrochloric acid by stirring 20 min. The oligomer was separated using a separatory funnel, and further washed with equal parts by volume deionized water three times. After each wash, the aqueous/hydrocarbon mixture was placed in a separatory funnel and settled for at least 5 min. After the final water wash, the oligomer/NAO mixture was dried with MgSO$_4$ and filtered.

The weight of reaction product before washing and after washing were measured to determine the weight loss of product due to washing. The hydrocarbon product was analyzed for aluminum (Al) content to determine any residual ionic liquid catalyst is still remaining. The whole experiments were done in duplicate and the results are reported in Table 3.

TABLE 3

C$_{16}$ NAO Oligomerization with Ionic Liquid Catalyst and
Ionic Liquid Catalyst Removal via in Aqueous Wash

|  | Example 3-1 | Exmple 3-2 |
|---|---|---|
| Oligomerization Reactor volume, cc | 300 | 300 |
| Residence time, min | 10 | 10 |
| Reactor Pressure, psi | 100 | 100 |
| Reactor Temp., °C. | 130 | 130 |
| Conversion of C$_{16}$ NAO, wt % | 40.0 | 42 |
| Oligomer/NAO before wash, g | 856.0 | 840.9 |
| Oligomer/NAO after wash, g | 793.3 | 794.1 |
| Hydrocarbon product recovered, wt % | 92.7% | 94.4% |
| Product weight-loss upon washing, wt % | 7.3% | 5.6% |
| Residual Al in hydrocarbon product, ppm | 30.7 | 25.1 |

This aqueous wash process showed high weight-loss during the washing and drying steps, 5.6-7.3 wt % of material was lost. With the total number of 4 washings, the amount of waste water generated was 4 times of the volume of the reaction production. In addition, about 5-10 wt % of waste MgSO$_4$ dryerant waste was generated. The hydrocarbon product still contains 25-30 ppm of residual Al coming from hydrolyzed ionic liquid catalyst.

Example 4: Olefin Oligomerization and Ionic Catalyst Removal with Silica Gel (Invention)

The olefin oligomerization reaction procedure of Example 3 was used to produce the oligomer reaction products of Examples, 4-1 and 4-2, except the reaction temperature. n-Hexadecene normal alpha olefin (C$_{16}$ NAO) was oligomerized using [BuPy][Al$_2$Cl$_7$] ionic liquid catalyst from Example 1-1 at 180 and 78° C. Oligomerization was run in a continuous unit with 0.2 vol % of ionic liquid catalyst.

A silica gel (Absorbent 1) with the mesopore diameter of 69.5 Å, mesopore volume of 0.48 cc/g and 454 m$^2$/g surface area was used for this example.

For Example 4-1, 1310.54 g of reaction product containing the ionic liquid catalyst and the hydrocarbon phase with unreacted monomer and oligomers was poured in a 2 L beaker, 68.75 g of silica gel (5 wt %) was added, and the mixture was stirred for 5 minutes. Then, the mixture was filtered in a Buchner funnel to filter out the silica gel containing ionic liquid catalyst and 1310.54 g of bright light-yellow colored hydrocarbon filtrate was recovered. The hydrocarbon product was analyzed for Al and N content to determine any residual ionic liquid catalyst is still remaining. The results are summarized in Table 4.

Another experiment (Example 4-2) also used the similar experimental procedures and the results are summarized in Table 4.

TABLE 4

C$_{16}$ NAO Oligomerization with Ionic Liquid Catalyst and
Ionic Liquid Catalyst Removal via Silica Gel Treatment

|  | Example 4-1 | Example 4-2 |
|---|---|---|
| Oligomerization Reactor volume, cc | 300 | 300 |
| Residence time, min | 10 | 10 |
| Reactor Pressure, psi | 100 | 100 |
| Reactor Temp., °C. | 180 | 78 |
| Conversion of C$_{16}$ NAO, wt % | 42 | 53 |
| Oligomer/NAO before silica-gel treating, g | 1374.96 | 756.57 |
| wt. silica gel, g | 68.75 | 37.82 |
| wt % silica for catalyst removal treatment | 5.0 w % | 5.0 wt % |
| Oligomer/NAO after silica-gel treating, g | 1310.54 | 723.9 |
| Hydrocarbon product recovered, wt % | 95.3% | 95.7% |
| Product weight-loss upon washing, wt % | 4.7% | 4.3% |
| Residual Al in Hydrocarbon Product, ppm | <2.1 | <2.1 |
| Residual N in Hydrocarbon Product, ppm | <0.3 | <0.3 |

The oligomer reaction products as formed were semi opaque light to dark brown liquids. Products after the silica-treatment and filtration were clear. Only one treatment with silica gel was needed. The amounts of hydrocarbon product recovered were 95.3 and 95.7%, which are higher than the finishing step with water quenching. The analysis of the residual trace metals shows that the amount of the residual ionic catalyst in the hydrocarbon are below the detection level.

Comparison data of oligomer products washed in water versus silica gel filtration set forth in Tables 3 and 4 clearly show that the silica gel finishing process has many advantages. The silica gel finishing process eliminated hazardous water generation, lower the loss of hydrocarbon product, simplified the process with lesser number of steps, and then produced better hydrocarbon product with lesser impurity.

Example 5: Olefin Oligomerization of $C_{16}$ NAO with Ionic Coordination Complex Catalyst of $AlCl_3$ and Acetamide and Removal of the Ionic Coordination Complex Catalyst with Silica Gel (Invention)

1-hexadecene was oligomerized in the presence of ionic coordination complex catalyst of Example 2-1 (Acetaminde-$AlCl_3$). A three-neck, 2 L round bottom flask equipped with a magnetic stir bar, a dropping funnel and a reflex condenser was prepared. 466.8 g of 1-hexadecene was loaded to the flask and a very small purge of dry nitrogen gas was applied while heating the liquid to 150° C. Once the round bottom flask contents reached thermal equilibrium, 2.0 g (~0.25 vol %) of Acetaminde-$AlCl_3$ ionic coordination complex from Example 2-1 was added dropwise for 10 minutes interval.

After the addition, the oligomerization reaction continued for 30 more minutes to produce the reaction mixture.

The product was treated with 5 wt % silica-gel (Adsorbent 1) to remove the catalyst residue. The final product shows 69.2% conversion of 1-hexadecene and 64% dimer selectivity.

Example 6: Solid Adsorbent Testing for Removal of Ionic Liquid Catalyst

In addition to Adsorbent 1, six other adsorbent materials were tested to identify the preferred adsorbents for the treating of the reaction mixture. Properties of the adsorbents are summarized in Table 5. $N_2$ adsorption test determined the total surface area, total pore volume for pores in the range of 0-1000 Å, and mesopore volume for pores in the range of 25-1000 Å, and the mean mesopore diameter.

Adsorbent 2 and Adsorbent 3 are high surface area (>700 $m^2/g$) silica gel with very small pores, in that the mean mesopore diameters are 17.9 and 18.5 Å, respectively. The mesopore volumes of Adsorbent 2 and Adsorbent 3 are very low (0.04 and 0.05 cc/g) while the total pore volumes are substantial amounts of 0.39 and 0.40 cc/g, indicating most of the pores are less than 25 Å diameter.

Adsorbents 4 through 6 are silica gels with high mesopore volume (0.73-1.87 $m^2/g$) and large mean mesopore diameters (104-416 Å) while having lower surface areas (280-310 $m^2/g$).

Absorbent 1 has the intermediate size mean mesopore diameter of 69.5 Å, mesopore volume of 0.48 cc/g, and 454 $m^2/g$ surface area.

Adsorbent 7 is an alumina beads with 0.42 cc/g of mesopore volume and 201 $m^2/g$ surface area.

To understand the impact of solid adsorbent properties in removing the ionic catalyst, 160 g of the reaction mixture from Example 5 was taken and treated with solid adsorbents for removal of the catalyst from the reaction mixture.

20 g each of the reaction mixture from Example 5 was loaded to eight 40 mL centrifuge vials. 2.0 g (10 wt %) of solid adsorbent from Table 4 was loaded (Adsorbent 2 through Adsorbent 7) to each vial. One of the vial did not have the solid adsorbent, as the base case, and was subjected to the same subsequent treatments. These eight vials were shaken with a mechanical shaker at 2,000 RPM for 1 hour for extraction. Then the vials were centrifuged for 1 hour at 2,400 RPM to precipitate the ionic catalyst and solid adsorbent to the bottom of the vial. The supernatant hydrocarbon was removed carefully and analyzed for the aluminum (Al) content by ICP analysis and for the nitrogen (N) content by combustion analysis with chemiluminescence detection. The analysis data are summarized in the table below.

TABLE 5

Physical Properties of Silica Gel Solid Adsorbents Tested

| $N_2$ Adsorption Test | Adsorbent 1 High Purity Silica-Gel with large pore diameter | Adsorbent 2 High Purity Silica-Gel with low mesopore volume | Adsorbent 3 High Purity Silica-Gel with low mesopore volume | Adsorbent 4 High Purity Silica-Gel with high mesopore volume | Adsorbent 5 High Purity Silica-Gel with high mesopore volume | Adsorbent 6 High Purity Silica-Gel with high mesopore volume | Adsorbent 7 High Purity Alumina Sphere high mesopore volume |
|---|---|---|---|---|---|---|---|
| BET Adsorption Surface Area, m2/g | 454 | 730 | 749 | 309 | 284 | 292 | 201 |
| Mean Mesopore Diameter, Å | 69.5 | 17.9 | 18.5 | 131 | 104 | 416 | 97 |
| Total Pore Volume, cc/g | 0.70 | 0.39 | 0.40 | 1.08 | 0.87 | 2.04 | 0.52 |
| Pore volume, 0-1000 Å, cc/g | 0.7 | 0.38 | 0.40 | 1.08 | 0.86 | 2.01 | 0.52 |
| Mesopore volume, 25-1000 Å, cc/g | 0.48 | 0.04 | 0.05 | 0.93 | 0.73 | 1.87 | 0.42 |

TABLE 6

Residual Catalyst Impurity in Hydrocarbon Phase After Silica Gel Solid Adsorbent Treating

|  | Base Case No solid adsorbent | Adsorbent 2 High Purity Silica-Gel with low mesopore volume | Adsorbent 3 High Purity Silica-Gel with low mesopore volume | Adsorbent 4 High Purity Silica-Gel with high mesopore volume | Adsorbent 5 High Purity Silica-Gel with high mesopore volume | Adsorbent 6 High Purity Silica-Gel with high mesopore volume | Adsorbent 7 High Purity Alumina Sphere high mesopore volume |
|---|---|---|---|---|---|---|---|
| $N_2$ Adsorption Test |  |  |  |  |  |  |  |
| Total Pore Volume, cc/g | — | 0.39 | 0.40 | 1.08 | 0.87 | 2.04 | 0.52 |
| Mesopore volume, 25-1000 Å, cc/g | — | 0.04 | 0.05 | 0.93 | 0.73 | 1.87 | 0.42 |
| Residual Al and N concentrations in the Hydrocarbon Phase after centrifuge |  |  |  |  |  |  |  |
| Al Concentration, ppm | 74.5 | 3.8 | 77.9 | <1.1 | <1.1 | <1.1 | >80 |
| N Concentration, ppm | 6.4 | <0.3 | 1.4 | <0.3 | <0.3 | <0.3 | 9.5 |

The results above clearly showed that Adsorbent 2 and Adsorbent 3 are inferior in removing the ionic catalyst residue, indicating that presence of high mesopore volume is desirable for treating of reaction mixture.

Adsorbent 7 is activated alumina with 0.42 cc/g of mesopore volume. However, to our surprise, the hydrocarbon product still contains high levels of Al and N, comparable to the base case where no adsorbent is used. Based on this, we concluded active silica gel is far preferred for removal of ionic catalyst than alumina. Also pore size of silica gel is important, and mesopores are needed to capture the ionic catalyst.

Example 7: Olefin Oligomerization of $C_{16}$ NAO with Ionic Coordination Complex of $AlCl_3$ and Acetamide and Removal of the Ionic Coordination Complex with Silica Gel (Invention)

1-hexadecene was oligomerized in a continuous unit in the presence of ionic coordination complex catalyst of Example 2-1. About 0.3 vol % of ionic complex catalyst was added to the $C_{16}$ NAO at 120-150° C. in 300 cc reactor with total residence time of 60 minutes. No additional HCl gas was added.

The oligomerization reaction product was treated with Adsorbent 4 silica-gel to remove the ionic catalyst.

TABLE 7

$C_{16}$ NAO Oligomerization with Ionic Complex Catalyst and Ionic Complex Catalyst Removal via Silica Gel Treatment

|  | Example 7-1 | Example 7-2 |
|---|---|---|
| Oligomerization reactor volume, cc | 300 | 300 |
| Residence time, min | 60 | 60 |
| Reactor pressure, psi | 100 | 100 |
| Reactor Temp., °C. | 122 | 150 |
| Conversion of $C_{16}$ NAO, wt % | 59 | 63 |
| wt % silica for catalyst removal treatment | 5.0 wt % | 7.0 wt % |

TABLE 7-continued $C_{16}$ NAO Oligomerization with Ionic Complex Catalyst and Ionic Complex Catalyst Removal via Silica Gel Treatment

|  | Example 7-1 | Example 7-2 |
|---|---|---|
| Hydrocarbon product recovered, wt % | 94.5 | — |
| Residual Al in hydrocarbon product, ppm | <2.1 | <2.1 |
| Residual N in hydrocarbon product, ppm | <0.3 | <0.3 |

The analysis of the residual trace Al and N in the oligomer reaction product, reported in Table 7, clearly shows that the amount of the residual ionic catalyst in the hydrocarbon are below the detection level.

Example 8—Premium Low-Viscosity Base Oil Manufacturing Process for High Yield and Superior Product Properties In order to produce premium low-viscosity base oil, a systematic study was conducted to identify preferred oligomerization and hydrogenation catalysts. Also the processing conditions for the oligomerization and hydroisomerization steps were optimized.

1-hexadecene ($C_{16}$ NAO) was oligomerized either in a batch unit or a continuous unit in the presence of ionic catalyst. Process conditions for the oligomerization step is summarized in Table 8. Addition of anhydrous HCl gas was required for the ionic liquid catalysts to increase the yield of the low-viscosity base oil, while no addition of HCl gas was needed for ionic coordination complex catalyst. The oligomerization reaction products were either washed with water or treated with silica-gel to remove the residual ionic catalyst in the products.

The purified oligomer products from Examples 8-1 and 8-2 were hydrogenated with a Pt,Pd/alumina catalyst in a batch unit for 6 hours of residence times to produce completely saturated hydrocarbon products. The purified oligomer products from Examples 8-3 and 8-4 were hydroisomerized with a Pt/zeolite/alumina catalyst to produce completely saturated hydrocarbon products. Then each hydrogenated whole liquid product was distilled to produce three fractions, 700° F.⁻ light fraction, low-viscosity base oil cut (700-910° F.) and high-viscosity base oil cut (910° F.+), and the base oil properties were measured. The process performance summary and final base oil properties are summarized in Table 8.

TABLE 8

Premium Base Oil Manufacturing Process for Superior Product Properties
Physical Properties Premium Base Oil Made from $C_{16}^=$ NAO

|  | Example 8-1 Comparative Example | Example 8-2 Comparative Example | Example 8-3 Invention | Example 8-4 Invention |
|---|---|---|---|---|
| Oligomerization Process with Ionic Catalyst | [BuPy][Al$_2$Cl$_7$] Ionic liquid, Example 1-1 | [BuPy][1.8 AlCl$_3$] Ionic liquid, Example 1-2 | [BuPy][Ga$_2$Cl$_7$] Ionic liquid, Example 1-3 | Urea-AlCl$_3$ Ionic complex, Example 2-2 |
| Olefin:HCl molar Ratio | 60:1 | 60:1 | 60:1 | No HCl |
| Oligomerization Method | Batch 0.5 vol % cat | Continuous 0.2 vol % cat | Continuous 0.2 vol % cat | Continuous 0.1 vol % cat |
| Oligomerization Temp, °C. | 100 | 130 | 130 | 150 |
| Residence Time, min | 30 | 10 | 20 | 60 |
| Pressure, psig | 0, atmospheric | 100 | 100 | 100 |
| NAO Conversion, wt % | 47 | 41 | 32 | 50 |
| Oligomer Product Selectivity | | | | |
| $C_{16}$-Chloride, wt % | 7 | 2 | 6 | 0.6 |
| Low-Vis Oil, wt % | 40 | 52 | 73 | 70.1 |
| High-Vis Oil, wt % | 53 | 46 | 21 | 29.3 |
| Finishing Step | Hydrogenation with Pt, Pd/Al$_2$O$_3$ catalyst | | Hydroisomerization with Pt/zeolite catalyst | |
| Finishing Temp, °C. | 300 | 250 | 288 | 277 |
| Pressure, psig | 600 | 800 | 600 | 600 |
| Residence time or space velocity (1/hr) | 6 hr batch | 6 hr batch | 0.5 LHSV | 0.25 LHSV |
| Total Lube Yield, % | 100 | 100 | 92 | 93 |
| Low-Viscosity Oil Properties | | | | |
| Viscosity at 100° C. | 4.6 | 4.3 | 3.89 | 4.18 |
| Viscosity Index | 164 | 151 | 134 | 133 |
| Pour Point, °C. | −10 | −6 | −47 | −45 |
| Cloud Point, °C. | 11 | 0 | −48 | −38 |
| Cold Crank Simulator (CCS) Viscosity at −30° C., cP | High, cannot measure | High, cannot measure | 640 | 878 |
| CCS Viscosity at −35° C., cP | — | — | 1302 | 1429 |
| Noack volatility, % | 5.0 | 5.5 | 13.2 | 7.4 |
| Mini-rotary viscometer viscosity at −40° C., cP | High, cannot measure | High, cannot measure | 2,006 | 2369 |
| Mini-rotary viscometer yield stress at −40° C. | — | — | No yield stress | No yield stress |
| High-Viscosity Oil Properties | | | | |
| Viscosity at 100° C. | 13.0 | 11.5 | 10.1 | 11.0 |
| Viscosity Index | 157 | 152 | 142 | 140 |
| Pour Point, °C. | 1 | −6 | −27 | −26 |
| Cloud Point, °C. | 2 | −4 | −22 | −25 |

Examples 8-1 through 8-4 clearly show that olefin oligomerization process using an ionic catalyst is very effective, only 0.1 to 0.5 vol % of ionic liquid catalyst is needed to convert substantial conversion of the olefins. However, in order to maximize the low-viscosity base oil yield, the catalyst choice and process conditions play very important role.

Comparison of Examples 8-1 and 8-2 show that the [BuPy][1.8 AlCl$_3$] catalyst operating at a higher temperature (130° C.) is preferred over the [BuPy][Al$_2$Cl$_7$] operating at 100° C. The low-viscosity base oil selectively was increased significantly with the use of the lower Lewis acidity catalyst, [BuPy][1.8 AlCl$_3$], and operating at a higher temperature (40 wt % at 100° C. vs. 52 wt % at 130° C.).

The hydrogenation finishing step of the oligomer products from Examples 1 and 2 with Pt,Pd/alumina catalyst, which has no strong acidity, does not crack the oil and the yield of the finished lube is about 100%. The hydrogenated $C_{16}$ oligomers (Examples 8-1 and 8-2) show excellent viscosity index and Noack volatility. However, the low-viscosity oils show poor low temperature behaviors (poor pour and cloud points, and poor cold crack simulator viscosity). These low-viscosity oils are far from meeting the target properties of the premium base oil shown in Table 1.

Example 8-2 low-viscosity base oil property results in Table 8 indicate that oligomerization at a high temperature of 130° C. improved the low temperature properties of the finished base oil somewhat while decreasing the viscosity index within the desirable range. The results show that some isomerization of hydrocarbon back-bone is happening during the oligomerization at high temperature of 130° C. or higher.

We conducted more oligomerization runs at 150 and 180° C. (data not shown in Table 8). With 180° C. oligomerization, the finished low-viscosity base oil showed −20° C. pour point and −5° C. cloud point. These improvements allow the finished base oil closer to meet the target properties of the premium base oil shown in Table 1, but not quite all the way meeting the targets. Thus, further improvement of base oil properties during the finishing step is required for $C_{16}$ NAO based low-viscosity base oil production.

Example 8-3 shows the performance of [BuPy][Ga$_2$Cl$_7$] ionic liquid catalyst for oligomerization. Compared to the AlCl$_3$ containing ionic liquid catalyst analog, the GaCl$_3$ containing ionic liquid catalyst showed the excellent selectivity for low-viscosity base oil (52% vs. 73% for Example 8-2 vs. 8.3) while the $C_{16}$ NAO conversion activity is lower (41% vs. 32% for Example 8-2 vs. 8.3).

The oligomer product made with the [BuPy][Ga$_2$Cl$_7$] ionic liquid catalyst was hydroisomerized with a Pt/zeolite/Al2O3 catalyst. Example 8-3 showed that with the hydroisomerization finishing at 288° C., excellent low-vis base oil with pour point of −47° C., cloud point of −48° C., 1320 cP CCS viscosity at −35° C. and passing mini-rotary viscometer (MRV) yield stress test. The base oil yield was decreased to 92%. This results clearly show that hydroisomerization finishing is a very powerful way to improve the low-viscosity base oil prepared by $C_{16}$ NAO dimerization and fully hydrogenate the product at the same time. No additional hydrogenation step was required.

The hydroisomerization finishing step with a zeolite catalyst cracks some of hydrocarbon molecules to lighter product (offgas, gasoline and diesel range product) and this is undesirable since it lowers the base oil yield. Since the cracking is increased with higher temperature, it is desirable to hydroisomerize at the lowest temperature or mildest condition possible while meeting product requirements. High temperature oligomerization at 130-200° C. range provides some isomerization of the oligomer structure and allows reduced severity in the hydroisomerization step, and improves the overall low-viscosity base oil yield.

Example 8-4 shows that the oligomerization process was further improved with ionic complex catalyst, Urea-AlCl$_3$ catalyst. Compared to the AlCl$_3$ containing ionic liquid catalyst (Example 8-2), the ionic complex catalyst showed the excellent selectivity for low-vis base oil (61% vs. 70% for Example 8-2 vs. 8.4) and at the same time higher $C_{16}$ NAO conversion (41% vs. 50% for Example 8-2 vs. 8.4). The selectivity of the Urea-AlCl$_3$ ionic complex catalyst is as good as that of GaCl$_3$ containing ionic liquid catalyst while the conversion activity is higher.

Another advantage of the Ionic complex catalyst (Example 8-4) is that the catalyst does not require anhydrous HCl gas addition, unlike the AlCl$_3$ containing ionic liquid catalysts requiring HCl (Examples 8-1 through 8.3). Eliminating the HCl addition will simplify the over process and make the process safer and economical. More importantly, the amount of $C_{16}$ chloride production is reduced significantly from 2-7% to 0.6 wt % in the oligomer reaction effluent. The reduction of $C_{16}$ chloride will make the recycling of the unreacted monomer and organic chloride reduction much easier.

The hydroisomerization of the oligomer product from Example 8-4 using a Pt/zeolite/Al$_2$O$_3$ catalyst produced excellent low-vis base oil with pour point of −45° C., cloud point of −38° C., 1429 cP CCS viscosity at −35° C. and passing mini-rotary viscometer (MRV) yield stress test. With the mild hydroisomerization finishing step, the base oil yield was 93%.

In summary, our results in Table 8 shows that NAO dimerization process with an ionic catalyst improves with use of high temperature oligomerization at 130° C. or higher, use of an ionic liquid catalyst with lower Lewis acidity, such as [BuPy][1.8 AlCl$_3$] catalyst or [BuPy][Ga$_2$Cl$_7$] catalyst, or ionic complex catalyst. The produced oligomer is further processed by mild hydroisomerization finishing step to produce a high quality premium low-vis base oil. This olefin dimerization followed by hydroisomerization is an efficient way to synthesize quality low-vis base oil from high molecular weight NAO ($C_{14}$-$C_{24}$ NAO) while maximize the overall base oil yield and base oil product quality.

The invention claimed is:

1. A hydrophobic process for separating hydrocarbon stream containing oligomerization products from an liquid catalyst post oligomerization reaction comprising (a) reacting a olefin monomer and liquid catalyst in a reactor to form an oligomer, (b) contacting the mixture comprising liquid catalyst and formed oligomer with a silica gel wherein the silica gel is 1-20 wt % of the combination of said mixture and silica gel and a has mean mesopore diameter of 30 Å to 1000 Å (c) producing a hydrocarbon stream containing oligomer product with some residual liquid catalyst and the silica gel retaining the rest of liquid catalyst.

2. The process of claim 1 wherein the reactor is a continuous stirred vessel.

3. The process of claim 1 or 2 wherein the silica gel has a mesopore (25-1000 A) pore volume of 0.2 cc/g to about 2 cc/g.

4. The process of claim 1 or 2 wherein the silica gel has a surface area of 100 m2/g to 500 m2/g.

5. The process of claim 1 or 2 wherein the liquid catalyst is an ionic liquid catalyst or an ionic complex catalyst.

6. The process of claim 5, wherein the ionic liquid catalyst is N-butylpyridinium chloroaluminate.

7. The process of claim 5, wherein the ionic liquid catalyst comprises anhydrous metal halides and amine salts.

8. The process of claim 5, wherein the ionic complex catalyst is homogenous molten liquid at ambient temperature consists of anhydrous metal halides as a Lewis acid with donor molecules that act as a Lewis base.

9. The process of claim 8, wherein the homogenous molten liquid at ambient temperature consists of a 3:2 molar ratio of anhydrous Lewis acid metal halides and Lewis base.

10. The process of claim 9, wherein the anhydrous Lewis-acid halides are selected from the group consisting of AlCl3, GaCl3, InCl3, AlBr3, AlI3, GaBr3, GaI3, InBr3 and InI3 and the Lewis base is selected from the group consisting of lutidine, collidine, alkylpyridines, trioctylphosphine, alkylphosphines, trioctylphosphine oxide, alkylphosphine oxide, urea, thiourea, acetamide, dialkylacetamides, alkylamides, octanenitryl, alkylnitrile.

11. The process of claim 1 or 2 wherein the liquid catalyst contains a metal halide.

12. The process of claim 11, wherein the metal halide is AlCl3, AlBr3, GaCl3, GaBr3, InCl3, and InBr3.

13. The process of claim 1 wherein the residual liquid catalyst content in the hydrocarbon stream is less than 50 ppm.

14. The process of claim 1 where in a hydrocarbon product loss from the treatment is less than 10 wt % of the hydrocarbon product.

15. A process for the production of a base oil comprising
  (a) reacting a normal alpha olefin comprising C14-C24 NAO in the presence of an ionic catalyst at a temperature equal to or greater than 130° C. to produce a reaction mixture containing oligomers;
  (b) contacting the reaction mixture produced in (a) with a silica gel wherein the silica gel is 1-20 by wt % of the combination of said mixture and silica gel to produce a hydrocarbon phase containing oligomer product with less than 50 ppm residual ionic catalyst and the silica gel retaining the rest of the ionic catalyst;
  (c) separating the hydrocarbon phase in (b) to a light fraction containing unconverted NAO and organic chloride and the other fraction containing the oligomer product; recycling the light fraction containing unconverted NAO and organic chloride to the conversion reaction step of (a);

(d) hydroisomerizing the fraction containing oligomer product produced in (c) under H2 atmosphere with a catalyst containing metal and either a medium pore zeolite or silica-alumina;

(e) distilling and fractionating the hydroisomerized product of (d) to produce a light fraction up to 371° C., low-viscosity base oil in the 371-488° C. distillate, and high-viscosity base oil above 488° C., wherein the low viscosity base oil distillate has 3.5-4.6 cSt viscosity at 100° C., >130 Viscosity Index, <15% Noack volatility, <−20° C. pour and cloud points and cold crank simulator viscosity of <2500 cP at −35° C., where in the high viscosity base oil distillate has 4.7 cSt viscosity or higher at 100° C., >130 Viscosity Index, and <−10° C. pour point.

16. The process of claim 15 wherein the residual ionic catalyst content in the hydrocarbon stream in 15(b) is less than 50 ppm.

17. The process of claim 15 wherein the silica gel has a mean mesopore diameter of 30 Å to about 1000 Å.

18. The process of claim 15 wherein the silica gel has a mesopore pore volume of 0.2 cc/g to about 2 cc/g.

19. The process of claim 15 wherein the silica gel has a surface area of 100 m2/g to 700 m2/g.

20. The process of claim 15 where in a hydrocarbon product loss from the silica gel treatment is less than 10 wt % of the hydrocarbon product.

21. The process of claim 15 wherein the ionic catalyst is an ionic liquid catalyst or an ionic complex catalyst.

22. The process of claim 15 wherein the ionic catalyst contains a metal halide.

23. The process of claim 22, wherein the metal halide is AlCl3, AlBr3, GaCl3, GaBr3, InCl3, and InBr3.

24. The process of claim 15, wherein the C14 to C24 normal alpha olefin is derived from bio-based sources selected from the group consisting of natural triglycerides, fatty acids and fatty alcohols, wax cracking.

* * * * *